United States Patent [19]

Bonhard et al.

[11] 4,439,357

[45] Mar. 27, 1984

[54] PROCESS FOR OBTAINING HEPATITIS-SAFE, STERILE HEMOGLOBIN SOLUTIONS FREE OF PYROGENS AND STROMA

[75] Inventors: Klaus Bonhard, Hanau; Bertram Eichentopf, Bad Soden; Norbert Kothe, Kronberg, all of Fed. Rep. of Germany

[73] Assignee: Biotest-Serum-Institut GmbH, Frankfurt, Fed. Rep. of Germany

[21] Appl. No.: 404,197

[22] Filed: Jul. 30, 1982

[30] Foreign Application Priority Data

Aug. 4, 1981 [DE] Fed. Rep. of Germany ....... 3130770

[51] Int. Cl.$^3$ ..................... A61K 35/18; A61K 37/02; C07G 7/00; C07C 103/52
[52] U.S. Cl. .......................... 260/112 B; 260/112.5 R; 424/101; 424/177
[58] Field of Search .................... 260/112 B, 112.5 R; 424/101, 177

[56] References Cited

U.S. PATENT DOCUMENTS 3,864,478 2/1975 Bonhard .............................. 424/101
4,001,200 1/1977 Bonsen et al. ..................... 260/112.5
4,136,093 1/1979 Bonhard et al. ................. 260/112.5
4,336,248 6/1982 Bonhard et al. ..................... 424/101
4,376,727 3/1983 Sato et al. ......................... 260/112 B Primary Examiner—Howard E. Schain
Attorney, Agent, or Firm—Sprung, Horn, Kramer & Woods

[57] ABSTRACT

A process for obtaining hepatitis-safe, sterile, pyrogen- and stroma-free hemoglobin solutions of low potassium content comprising stirring an erythrocyte concentrate with about 1 to 6-times its volume of an about 5 to 15% aqueous solution of a sugar, sugar alcohol or high-molecular-weight colloid, adjusting the pH of the resulting suspension to about 5 to 6.5 with an acid which is physiologically tolerable as salt, allowing the erythrocytes to settle, removing the supernatant from the sediments, adjusting the pH of the sediment to about 7 to 8, homogenizing the sediment, adjusting its hematocrit to about 55 to 60%, treating the mass with a dilute beta-propiolactone solution, hemolyzing the residual solids and forming a suspension thereof, contacting the suspension with a cation exchanger in H+ form until the pH has decreased to about 5 to 5.5 thereby to precipitate the stroma, separating from the liquid the cation exchanger and precipitated stroma, and adjusting the pH to about 7.2 to 7.6.

7 Claims, No Drawings

PROCESS FOR OBTAINING HEPATITIS-SAFE, STERILE HEMOGLOBIN SOLUTIONS FREE OF PYROGENS AND STROMA

Hemoglobin solutions in which the erythrocytes are largely undamaged can be produced economically in the amounts required for a variety of clinical uses by a process for the production of hepatitis-safe, sterile hemoglobin solutions of low potassium content which are free of pyrogens and stroma by the treatment of erythrocytes with betapropiolactone, hemolysis, treatment of the hemolyzate with a cation exchange resin in H+ form, quantitative separation of the stroma lipid and sterilization by filtration, in which the concentrated erythrocytes are stirred together with one to six times their volume of an aqueous, 5 to 15% solution of a sugar, sugar alcohol or colloid of high molecular weight, adjusting the pH of the suspension to from 5 to 6.5, and shutting off the stirrer and letting the erythrocytes settle out.

BACKGROUND

The invention concerns a method for obtaining hepatitis-safe, sterile, hemoglobin solutions free of pyrogens and stroma and having a low potassium content, by the treatment of erythrocytes with propiolactone, hemolysis, treatment of the hemolyzate with a cation exchange resin in H+ form, quantitative separation of the stroma lipid, and sterilization by filtration.

Hemoglobin solutions are capable of transporting oxygen in vivo independently of erythrocytes. In order for such solutions to be physiologically tolerable, however, it is necessary to remove as completely as possible the plasma and cell components of the blood from which the hemoglobin is released by hemolysis (plasma proteins, stroma, leucocytes, thrombocytes).

German Pat. No. 2,248,475 discloses a process for preparing such hemoglobin solutions, in which the separation of plasma proteins and erythrocytes is accomplished by floating the erythrocytes in physiological electrolyte solutions and then separating them by centrifugation in discontinuously operating centrifuges.

In "Appraisal of Hemoglobin Solution as a Blood Substitute" by Frank De Venuto, Harold J. Friedmann, J. Ryan Neville and Carl C. Peck, Surgery, Gynecology & Obstetrics, Sept. 1979, Vol. 149, p. 417–436, different methods are described whereby hemoglobin is obtained by crystallization.

Neither the discontinuous centrifugation (blood centrifuge) that is necessary for the washing of erythrocytes nor the dialysis that is necessary in crystallization processes are suitable procedures for the preparation of such large amounts of hemoglobin solution as would be needed for clinical use. Ordinary discontinuously operating centrifuges have a capacity, for example, of only about six liters. The use of a plurality of discontinuously operating centrifuges would be extremely uneconomical.

Washing erythrocytes with electrolyte solutions results in a high electrolyte content in the end product, which would be a disadvantage in the case of special applications, such as the perfusion of coronary heart vessels (cardioplegia) in open-heart surgery.

With the exception of the process described in German Pat. No. 2,248,475, the transmission of serum hepatitis cannot be entirely prevented in any of the other methods of hemoglobin production. However, even the method of sterilization with β-propiolactone described in German Pat. No. 2,248,475 has the disadvantage that this treatment is the first step in the process, which means that the amount of β-propiolactone used acts on any residual amounts of plasma proteins remaining, depending on the method used in preparing the erythrocyte concentrate. Thus a different β-propiolactone concentration acts on the erythrocytes, depending on the amount of residual plasma.

Continuously operating centrifuges are known for the separation of large amounts of blood into cell components and plasma, and they are used, for example, in slaughterhouses for the recovery of a hemoglobin-free plasma. In this process, however, the erythrocytes are so severely damaged that they are nearly entirely destroyed, especially if they pass repeatedly through the centrifuge. Therefore, this continuous centrifugation is not appropriate for the washing of erythrocytes.

THE INVENTION

It is the object of the invention to devise a process for the recovery of hepatitis-safe, sterile hemoglobin solutions free of pyrogens and stroma, by means of which such hemoglobin solutions can be prepared for different applications in an economical manner, in the large amounts that are required for clinical applications, and which will permit the erythrocytes to be washed without damage.

This object is achieved by the invention by the fact that an erythrocyte concentrate is stirred with one to six times its volume of an aqueous 5 to 15% solution of a sugar, sugar alcohol or high-molecular-weight colloid, the pH of the suspension is adjusted to 5 to 6.5 with an acid which is physiologically tolerable in salt form, the stirrer is shut off and the erythrocytes are allowed to settle, the supernatant is removed, the above washing process is repeated one or more times on the erythrocyte sediment if desired, the pH of the sediment is adjusted to 7 or 8, the sediment is homogenized and its hematocrit is adjusted to 55 to 60%, it is treated for several to as much as 25 minutes with a dilute solution of β-propiolactone, and then the above washing process is repeated one or more times, and the hemolyzate obtained by stirring the erythrocytes into distilled water is treated with a cation exchanger in H+ form until the pH has fallen to 5.0 to 5.5, and is freed of the resin and from the precipitated mass of stroma by centrifugation and/or filtration, the pH is adjusted to 7.2 to 7.6, and the desired hemoglobin concentration is established, the additives required for the intended application are added, and the mixture is sterilized by filtration.

Erythrocytes in a suspension have a tendency to settle. This phenomenon is called *sedimentation,* and is used in diagnostics to detect inflammatory processes. Normal blood sedimentation amounts to approximately 5 mm per hour. By the addition of various substances, erythrocyte sedimentation can be accelerated. Examples of the use of sedimentation accelerators are described in the literature. For example, according to R. G. Strauss, "In Vitro Comparison of the Erythrocyte Sedimenting Properties of Dextran, Hydroxyethyl Starch and a New Low-Molecular-Weight Hydroxyethyl Starch", Vox Sang. 37:268-271 (1979)(3), colloids of high molecular weight are used for the preparation of concentrates of thrombocytes and leukocytes. According to O. Akerblom and C. F. Hoegman, "Progress in Freeze-Preservation of Red Blood Cells in Sweden", (Symposium on Deep-Freeze Preservation of Erythrocytes, Nov. 27–28, 1973, Frankfurt-on-Main)(4), sugar or sugar alcohols find use in the removal of glycerin from erythrocyte concentrates which are thawed after deep-freeze storage. Here, mixtures of glucose and fructose in different concentrations are used, and certain ratios of admixture are given. The electrolyte concentration is limited to 10 to 15 millimoles per liter. Disclosure 4 thus reveals the use of sugar or sugar alcohols as sedimentation accelerators, but the sedimentation method using these accelerators has never since been tested (20 years) in the preparation of hemoglobin solutions, because the persons skilled in the art of the preparation of oxygen transporting hemoglobin solutions do not look for ideas in the field of endeavor of producers of preserved blood who deal with the deep-freeze storage of erythrocytes.

In the process of the invention, it has been found, in contrast to the above-mentioned citations from the literature, that the sedimentation can be performed with only one sugar or sugar alcohol. A specific mixture of several sugars is not necessary in the process of the invention and, with an eye to the variety of applications explained above, it is not desirable.

Likewise, a single sugar concentration will suffice for the performance of a number of sedimentations, if the pH levels are correspondingly low.

In accordance with the invention, erythrocyte concentrates which are no longer suitable for transfusion because they have exceeded the maximum storage time, are pooled thout regard to blood group and treated by stirring with one to six times, preferably 2.5 times, the volume of a 5 to 15%, preferably 10%, sugar or sugar alcohol solution or of a colloid of high molecular weight. Glucose, mannitol, fructose, sorbitol, xylitol and disaccharides such as saccharose and maltose can be used as sugars and sugar alcohols. Suitable colloids of high molecular weight are hydroxyethyl starch or dextran. The pH of the suspension is adjusted to 5 to 6.5, preferably 5.4, with a physiologically tolerable acid, such as for example 1N hydrochloric acid. The pH of 5.4 has proven desirable especially in the case of a high electrolyte content in the starting material.

The temperature of the suspension is preferably maintained at 2° to 18° C., 10° C. being especially preferred, during the entire process. After the stirrer is shut off, the erythrocytes are allowed to settle preferably for from 15 minutes to 10 hours, 60 minutes being especially preferred. After sedimentation, the supernatant is removed, the volume of the sediment is measured, and the washing process is repeated. The erythrocyte sediment thus obtained is disaggregated by adjusting the pH to 7–8, preferably to 7.4, and homogenized by stirring. The hematocrit of the sediment is adjusted with the sedimentation solution to 55 to 60%. Then a $\beta$-propiolactone solution is quickly added, with stirring. Preferably, 0.166 liter of a 1.5% $\beta$-propiolactone solution freshly prepared with the sedimentation solution is used per liter of sediment. The two or more washings of the erythrocytes before the addition of $\beta$-propiolactone has the advantage over formerly described processes that no appreciable amounts of residual plasma are present, which might affect the sterilizing action of the $\beta$-propiolactone. This means that an always uniform concentration of $\beta$-propiolactone acts on a specific volume of erythrocytes.

After a period of action of 20 minutes, the $\beta$-propiolactone has reacted virtually completely. For the removal of the reaction products, one or more, preferably three, washings are performed as described above. The washed erythrocytes are hemolyzed by the addition of distilled water. The hemolysis is performed preferably by the addition of 1.5 to 5 times the volume of distilled water, 2.5 times being preferred, at pH 7. For the separation of the stroma, the hemolyzate is treated with a cation exchange resin in H+ form, desirably in amounts of 50 to 150, preferably of 80,mval/1, until the pH has decreased to 5.0 to 5.5, preferably 5.1. Especially suitable cation exchange resins are acid polystyrene sulfonate cation exchangers having an exchange capacity of 4 to 5 mval per gram of dry resin, and other polystyrene resins, which differ substantially as regards thermal stability, grain size, pigment content and exchange capacity. Further information can be found in K. Dorfner: "Ionenaustauscher", Walter de Gruyter, Berlin (1964).

After increasing the pH to 5.2 to 6, preferably 5.65, the ion exchanger is filtered out and the precipitated stroma is removed by continuous centrifugation and/or filtration. After adjusting the pH to 7.2 to 7.6, preferably 7.4, and adjusting the desired hemoglobin concentration, and, if desired, the addition of additives, the solution is again centrifuged and/or prefiltered prior to filtration.

Depending on the application, additives can be electrolytes or effectors for improving the oxygen yield of the hemoglobin, such as, for example, 2,3-diphosphoglycerate, pyrridoxal phosphate or inositol hexaphosphate.

By the method of the invention, any desired amounts can be prepared in a single batch, depending on the size of the sedimentation vessel and the available centrifuge capacity.

The product in accordance with the invention can be used, depending on the nature of the additives, for perfusion of the coronary vessels of the heart (cardioplegia) or of severed or crushed extremities, or it can be used as a starting product for the preparation of chemically modified hemoglobin solutions for infusion purposes, as described, for example, in German Pat. Nos. 2,449,885 or 2,617,822.

Thus, for example, a cardioplegic solution requires a low sodium and glucose content, while for perfusion of the extremities, physiological sodium levels and a high glucose content are desired.

According to the present-day state of knowledge, human erythrocytes must be used for application to the human body.

The following examples illustrate the practice of the present invention.

EXAMPLES

EXAMPLES 1

111 erythrocyte concentrates were pooled in a refrigerated 160-liter VA steel vessel with stirrer. The resulting volume was 26 liters. The temperature was kept at approximately 10° C. throughout the process. After the addition of 65 liters of 10% glucose solution and adjustment of the pH to 5.4, stirring was performed for 10 minutes. Then the mixture was allowed to settle for 45 minutes and the supernatant was aspirated out. The sediment contained 18.4% hemoglobin and the hematocrit was 49%. For the second washing, 112 liters of 10% glucose solution were added, the pH was corrected to 5.4, the mixture was stirred for 10 minutes, and sedimentation was again performed for 45 minutes.

The sediment (28 l, hematocrit 67%, hemoglobin 25.5%), after the pH had been raised to 7.4 with 1N sodium hydroxide, was homogenized with stirring. The hematocrit was adjusted to 55-60% (59%) with 10% glucose solution. Then 4.9 liters of 1.5% beta-propiolactone solution in 10% glucose was rapidly added, and allowed to act, with stirring, for 20 minutes, while the pH decreased to 7.14. For the third sedimentation, 10% glucose solution was added to make 100 liters and the pH was again adjusted to 5.4. The sedimentation was performed, and also the 4th and 5th sedimentation, in the manner described above. The volumes of the third, fourth and fifth sediments amounted to 31, 27 and 24 liters. The pH of the fifth sediment was adjusted with 1N sodium hydroxide to 7.0. The hemolysis was performed by mixing with 60 liters of distilled water. After 30 minutes of intense stirring, a test was performed to assure that the hemolysis was complete. For the removal of the stroma, first 143 g of sodium chloride, then 2.94 kg of high-purity (pA quality) cation exchange resin in $H^+$ form, with a capacity of 4 mval per gram of dry substance, with a divinylbenzene content of 8% in the preparation of its polystyrene matrix, and with a grain size between 297 and 840 $\mu$m, was added. The pH diminished constantly.

When a pH of 5.1 was reached, 2.5 liters of 1N sodium hydroxide was slowly added, with stirring. The pH rose to 5.65. The ion exchanger was separated with a coarse sieve, and the precipitated stroma was removed by continuous centrifugation at approximately 5000 G. The pH of the solution thus clarified was adjusted to 7.4 by the addition of 1.4 liters of 1N sodium hydroxide. 247 g of sodium chloride, 110 g of sodium bicarbonate and 715 g of glucose were added, and the mixture was again centrifuged.

The concluding sterilization by filtration was performed in two ways, namely first through deep filter layers, then through membrane filters such as are commonly used for this kind of sterilization.

Yield: 60 liters
Hemoglobin: 8%

EXAMPLE 2

122 erythrocyte concentrates were pooled in the same manner as in Example 1. The volume amounted to 29 liters, the temperature to 10° C. After the addition of 72.5 liters of 10% mannitol solution and adjustment of the pH to 5.4 with 1N hydrochloric acid, the mixture was stirred for 10 minutes. The sedimentation time was 45 minutes; the sediment contained 22.8% hemoglobin and had a hematocrit of 45%. The second washing was performed with 82.5 liters of 10% mannitol solution. The volume of the sediment was 24 liters. The treatment with beta-propiolactone was performed in the same manner as in Example 1. The amounts of 10% mannitol solution for the third, fourth and fifth washings were 75, 65 and 63 liters, the sediment volumes 26, 25 and 17 liters. The rest of the procedure was as in Example 1.

Yield: 35 liters
Hemoglobin content: 9%

EXAMPLE 3

1st Washing Solution:
  6% hydroxyethyl starch
  in 0.9% sodium chloride solution
2nd Washing Solution:
  6% hydroxyethyl starch
  in 1.3% sodium bicarbonate solution One liter of washing solution 1 was placed in a ten-liter vessel and 7 erythrocyte concentrates (total approx. 1.7 l) were added, with stirring. Then an additional 2.5 liters of washing solution 1 was added to the erythrocyte suspension, so that the ratio of erythrocyte concentrate to the washing solution was 1:2. Within 75 minutes the cells settled out, resulting in a ratio of supernatant to the sediment of approximately 1:1. The supernatant was removed by aspiration, the sediment was resuspended with 3.5 l of washing solution 2, and then was left to settle for 60 minutes. The supernatant, which still contained 0.18% of protein, was removed. To the sediment, which had a hematocrit of 57.5%, 415 ml of washing solution 1, which contained 1.5% of beta-propiolactone, was added, and allowed to act for 20 minutes with stirring. Then washing solution 2 was added to make 6 liters.

After 60 minutes the supernatant, containing 0.15% of hemoglobin, was aspirated away and sedimentation with washing solution 2 was repeated. The procedure of Example 1 was then continued.

Yield: 5.5 liters
Hemoglobin: 7%

It is understood that the specification and examples are illustrative but not limitative of the present invention and that other embodiments within the spirit and scope of the invention will suggest themselves to those skilled in the art.

We claim:

1. A process for obtaining hepatitis-safe, sterile, pyrogen- and stroma-free hemoglobin solutions of low potassium content comprising stirring an erythrocyte concentrate with about 1 to 6-times its volume of an about 5 to 15% aqueous solution of a sugar, sugar alcohol or high-molecular-weight colloid, adjusting the pH of the resulting suspension to about 5 to 6.5 with an acid which is physiologically tolerable as salt, allowing the erythrocytes to settle, removing the supernatant from the sediments, adjusting the pH of the sediment to about 7 to 8, homogenizing the sediment, adjusting its hematocrit to about 55 to 60%, treating the mass with a dilute beta-propiolactone solution, hemolyzing the residual solids and forming a suspension thereof, contacting the suspension with a cation exchanger in $H^+$ form until the pH has decreased to about 5 to 5.5 thereby to precipitate the stroma, separating from the liquid the cation exchanger and precipitated stroma, and adjusting the pH to about 7.2 to 7.6.

2. A process according to claim 1, wherein the temperature is from about 2° to 18° C. during the process up until at least the cation exchanger treatment.

3. A process according to claim 1, wherein the pH of the suspension is adjusted to about 5.4 prior to the settling of the erythrocytes.

4. A process according to claim 1, wherein the erythrocytes are allowed to settle for from about 15 minutes to 10 hours.

5. A process according to claim 1, wherein the pH of the sediment is adjusted to about 7.4 prior to the beta-propiolactone treatment.

6. A process according to claim 1, wherein one additional washing of the erythrocyte sediment with solution of sugar, sugar alcohol or colloid is performed before the beta-propiolactone treatment, and, after the beta-propiolactone treatment but before the cation exchanger treatment, the solids are washed three times with solution of sugar, sugar alcohol or colloid.

7. A process according to claim 6, including the further step of sterile filtering the final solution.

* * * * *